(12) United States Patent
Su

(10) Patent No.: US 6,952,651 B2
(45) Date of Patent: Oct. 4, 2005

(54) METHODS AND APPARATUS FOR NUCLEIC ACID SEQUENCING BY SIGNAL STRETCHING AND DATA INTEGRATION

(75) Inventor: Xing Su, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 255 days.

(21) Appl. No.: 10/174,365

(22) Filed: Jun. 17, 2002

(65) Prior Publication Data

US 2003/0232346 A1 Dec. 18, 2003

(51) Int. Cl.[7] .............................................. G06F 19/00
(52) U.S. Cl. ............................ 702/20; 702/19; 702/22; 435/6
(58) Field of Search ........................ 702/19, 20; 435/6; 536/22.1; 436/518, 501

(56) References Cited

U.S. PATENT DOCUMENTS

| | | | |
|---|---|---|---|
| 4,874,492 | A | 10/1989 | Mackay |
| 5,061,067 | A | 10/1991 | Yamamoto et al. |
| 5,302,272 | A | 4/1994 | Klein |
| 5,538,898 | A | 7/1996 | Wickramasinghe et al. |
| 5,840,862 | A | 11/1998 | Bensimon et al. |
| 5,846,708 | A | 12/1998 | Hollis et al. |
| 6,054,327 | A | 4/2000 | Benismon et al. |
| 6,117,643 | A | 9/2000 | Simpson et al. |
| 6,146,227 | A | 11/2000 | Mancevski |
| 6,147,198 | A | 11/2000 | Schwartz |
| 6,201,896 | B1 | 3/2001 | Ishikawa |
| 6,225,055 | B1 | 5/2001 | Bensimon et al. |
| 6,265,153 | B1 | 7/2001 | Bensimon et al. |
| 6,274,320 | B1 | 8/2001 | Rothberg et al. |
| 6,280,939 | B1 | 8/2001 | Allen |
| 6,303,296 | B1 | 10/2001 | Bensimon et al. |
| 6,344,319 | B1 | 2/2002 | Bensimon et al. |
| 6,355,420 | B1 * | 3/2002 | Chan ............................. 435/6 |
| 2003/0059822 | A1 * | 3/2003 | Chan et al. ..................... 435/6 |

OTHER PUBLICATIONS

U.S. Appl. No. 60/322,981.*
Akeson et al., "Microsecond Time–Scale Discrimination Among Polycytidylic Acid, Polyadenylic Acid, and Polyuridylic Acid as Homopolymers or as Segments Within Single RNA Molecules," *Biophysical J.*, 77:3227–3233, 1999.

(Continued)

*Primary Examiner*—Marianne P. Allen
*Assistant Examiner*—Jerry Lin
(74) *Attorney, Agent, or Firm*—DLA Piper Rudnick Gray Cary US LLP

(57) ABSTRACT

The methods and apparatus 100 disclosed herein concern DNA sequencing. In some embodiments of the invention, the methods comprise measuring the distance between labeled nucleotides 220, such as nucleotides labeled with bulky groups. The methods may further comprise placing identical template DNA 200 into four reaction chambers 110, 120, 130, 140, each containing a different labeled nucleotide precursor, synthesizing complementary strands 230, 240, 250 and detecting labeled nucleotides 220. The distances between labeled nucleotides 220 may be used to construct 450 distance maps 310, 320, 330, 340 for each type of labeled nucleotide 220. The distance maps 310, 320, 330, 340 may be aligned 520 to obtain a nucleic acid sequence 210. Overlapping data analysis and frequency analysis may be used to construct 450 the distance maps 310, 320, 330, 340 and non-overlapping data analysis may be used to align 520 the distance maps into a sequence 210.

27 Claims, 3 Drawing Sheets

OTHER PUBLICATIONS

Murray et al., "Atomic Force Microscopy of Biochemically Tagged DNA," *Pro. Natl. Acad.. Sci. USA*, vol. 90, pp. 3811–3814, May 1993.

Hu, et al., "Imaging of Single Extended DNA Molecules on Flat (Aminopropyl)triethoxysilane Mica by Atomic Force Microscopy," *Langmuir The ACS Journal of Surfaces and Colloids*, vol. 12, No. 7, 1697–1699, 1996.

Bensimon et al., "Alignment and Sensitive Detection of DNA by a Moving Interface," *Science*, vol. 265(5181), 2096–2098, 1994.

Craighead, "Nanoelectromechanical Systems," *Science*, vol. 290, 1532–1535, 2000.

Eggers et al., "A Microchip for Quantitative Detection of Molecules Utilizing Luminescent and Radioisotope Reporter Groups," *BioTechniques*, vol. 17, No. 3, 516–524, 1994.

Foret et al., "On–line Fiber Optic UV Detection Cell and Conductivity Cell for Capillary Zone Electrophoresis," *Electrophoresis*, 7, 430–432, 1986.

Hirokawa et al., "The Separation Process in Isotachophoresis," *Journal of Chromatography*, 463, 39–49, 1989.

Kasianowicz et al., "Characterization of Individual Polynucleotide Molecules Using a Membrane Channel," *Pro. Natl. Acad. Sci. USA*, vol. 93. pp. 13770–13773, Nov. 1996.

"Nanopore Technology, Probing Polynucleotides with a Nanopore: High Speed, Single Molecule DNA Sequencing," Branton Lab—Nanapore Sequencing Description, 3 pages, downloaded from the internet on Feb. 3, 2002.

\* cited by examiner taacttgacctgagctagtagagctataggcgatagccctctaagcc ← 200
|||||||||||||||||||||||||||||||||||||||||||||||
attgaactggactcgatcatctcgatatccgctatcgggagattcgg ← 210

200
taacttgacctgagctagtagagctataggcgatagccctctaagcc
|||||||||||||||||||||||||||||||||||||||||||||||
attgaactggactcgatcatctcgatatccgctatcgggagattcgg
210

SEQUENCE LISTING

<160> NUMBER OF SEQ ID NOS: 2

<210> SEQ ID NO 1
<211> LENGTH: 47
<212> TYPE: DNA
<213> ORGANISM: Artificial
<220> FEATURE:
<223> OTHER INFORMATION: Synthetic Oligonucleotide

<400> SEQUENCE: 1
taacttgacc tgagctagta gagctatagg cgatagccct ctaagcc            47

<210> SEQ ID NO 2
<211> LENGTH: 47
<212> TYPE: DNA
<213> ORGANISM: Artificial
<220> FEATURE:
<223> OTHER INFORMATION: Synthetic Oligonucleotide

<400> SEQUENCE: 2
ggcttagagg gctatcgcct atagctctac tagctcaggt caagtta            47

METHODS AND APPARATUS FOR NUCLEIC ACID SEQUENCING BY SIGNAL STRETCHING AND DATA INTEGRATION

FIELD OF THE INVENTION

The present methods, compositions and apparatus relate to the fields of molecular biology and genomics. More particularly, the disclosed methods and apparatus concern nucleic acid sequencing.

BACKGROUND

The advent of the human genome project required that improved methods for sequencing nucleic acids, such as DNA (deoxyribonucleic acid) and RNA (ribonucleic acid), be developed. Many common diseases, such as cancer, cystic fibrosis and sickle cell anemia, are based at least in part on variations in DNA sequence. Determination of the entire 3,000,000,000 base sequence of the human genome has provided a foundation for identifying the genetic basis of such diseases. However, a great deal of work remains to be done to identify the genetic variations associated with each disease.

Existing methods for nucleic acid sequencing, based on detection of labeled nucleic acids that have been separated by size, are limited by the length of the nucleic acid that can be sequenced. Typically, only 500 to 1,000 bases of nucleic acid sequence can be determined at one time. This is much shorter than the length of the functional unit of DNA, referred to as a gene, which can be tens or even hundreds of thousands of bases in length. Using current methods, determination of a complete gene sequence requires that many copies of the gene be produced, cut into overlapping fragments and sequenced, after which the overlapping DNA sequences may be assembled into the complete gene. This process is laborious, expensive, inefficient and time-consuming.

More recent methods of nucleic acid sequencing, involving hybridization to oligonucleotide arrays of known sequences at specific locations on a chip, may be used to infer short nucleic acid sequences or to detect the presence of a specific nucleic acid in a sample. However, they are not suited for identifying long nucleic acid sequences.

BRIEF DESCRIPTION OF THE DRAWINGS

The following drawings form part of the present specification and are included to further demonstrate certain embodiments of the invention. Those embodiments may be better understood by reference to one or more of these drawings in combination with the detailed description of specific embodiments of the invention presented herein.

FIG. 2 Illustrates an exemplary method for constructing a base distance map for one type of labeled nucleotide 220, based on measured distances between labeled nucleotides 220 in a number of nucleic acid strands 230, 240, 250 that are complementary to the template nucleic acid 200. The distances between labeled nucleotides 220 may be compiled into a distance map (see FIG. 3. distance map 310, 320, 330, 340) for each type of nucleotides labeled as described herein. The sequence 210 of the complementary strand 230, 240, 250 is shown, along with exemplary locations for labeled nucleotides 220. As indicated 260, where identical nucleotides are located adjacent to each other, this will be detected as an increased frequency of labeling at that location.

FIG. 3 Illustrates an exemplary method of aligning four base distance maps 310, 320, 330, 340 into a sequence 210 of the complementary strand (see FIG. 2, complementary strand 230. 240. 250). The template nucleic acid 200 will be an exact complement of the determined sequence 210.

DESCRIPTION OF ILLUSTRATIVE EMBODIMENTS

The disclosed methods, compositions and apparatus 100 are of use for the rapid, automated sequencing of nucleic acids. In particular embodiments of the invention, the methods, compositions and apparatus 100 are suitable for obtaining the sequences 210 of very long nucleic acid molecules. Advantages over prior methods of nucleic acid sequencing include the ability to read long nucleic acid sequences 210 in a single sequencing run, greater speed of obtaining sequence 210 data (up to 3,000,000 bases per second), decreased cost of sequencing and greater efficiency in terms of the amount of operator time required per unit of sequence 210 data generated.

The following detailed description contains numerous specific details in order to provide a more thorough understanding of the disclosed embodiments. However, it will be apparent to those skilled in the art that the embodiments of the invention may be practiced without these specific details. In other instances, devices, methods, procedures, and individual components that are known in the art have not been described in detail herein.

Figure 1:
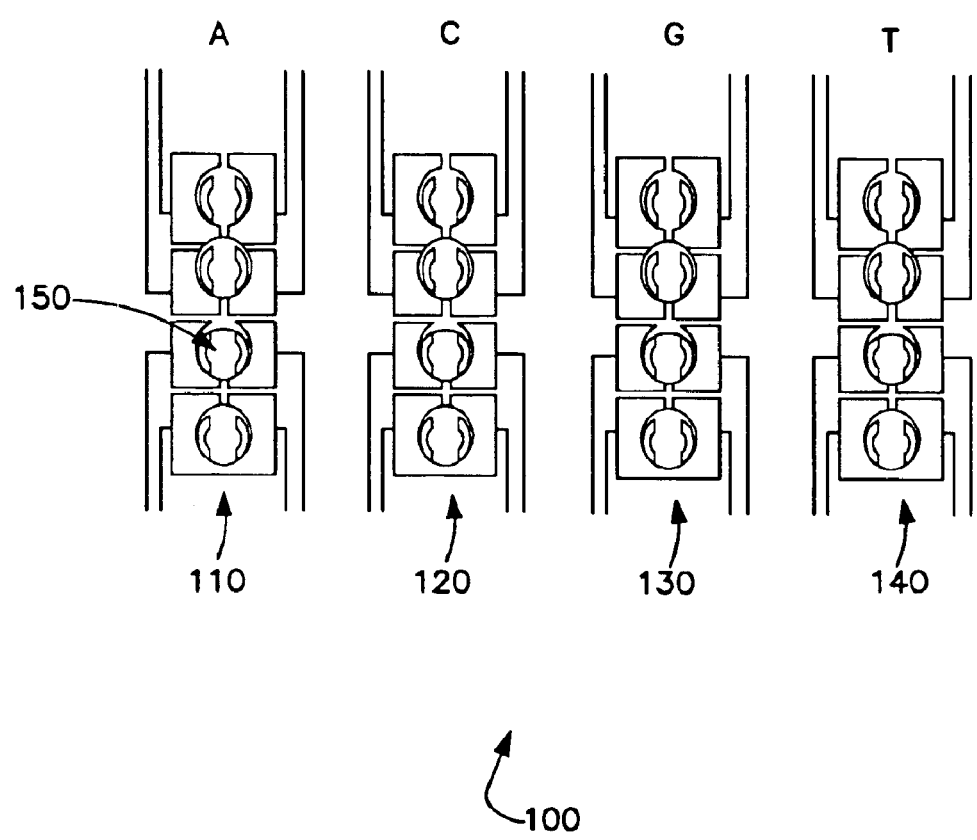
FIG. 1 illustrates an exemplary apparatus 100 (not to scale) for sequencing a nucleic acid template (see FIG. 2. nucleic acid template 200) by determining the distance between randomly labeled nucleotides. The apparatus includes four separate reaction chambers 110, 120, 130, 140 comprising nanopores 150.

Certain embodiments of the invention are illustrated in FIG. 1. FIG. 1 shows a method for nucleic acid sequencing comprising placing multiple copies of a template nucleic acid 200 into four reaction chambers 110, 120, 130, 140. Each of the reaction chambers 110, 120, 130, 140 contains a synthetic reagent, such as DNA polymerase, a primer complementary to the template molecule 200 and nucleotide precursors. In alternative embodiments of the invention the primer molecule can be labeled, allowing detection of a defined starting point for measurement of labeled nucleotide distances. The nucleotide precursors should include at least one molecule each of deoxyadenosine-5'-triphosphate (dATP), deoxyguanosine-5'-triphosphate (dGTP), deoxycytosine-5'-triphosphate (dCTP) and deoxythymidine-5'-triphosphate (dTTP) or deoxyuridine-5'-triphosphate (dUTP), although each reaction chamber will normally contain many molecules of each nucleotide precursor.

In addition, each chamber 110, 120, 130, 140 will contain one type of labeled nucleotide precursor. For example, the first reaction chamber 110 may contain labeled dATP, the second reaction chamber 120 may contain labeled dCTP, the third reaction chamber 130 may contain labeled dGTP and the fourth reaction chamber 140 may contain labeled dTTP. The addition of a small amount of one type of labeled nucleotide precursor in each of the four reaction chambers 110, 120, 130, 140 will produce randomly labeled complementary strands 230, 240, 250. In each chamber 110, 120, 130, 140, all complementary strands 230, 240, 250 may be labeled with the same type of nucleotide. In some embodiments of the invention, labeled nucleic acids 230, 240, 250 may be synthesized and analyzed in four reaction chambers 110, 120, 130, 140, with synthesis and analysis occurring in the same chamber. Alternatively, labeled complementary strands 230, 240, 250 may be prepared in one set of containers, for example in test tubes, microfuge tubes or microfiltration tubes, then separated from unincorporated nucleotides and analyzed in a set of chambers 110, 120, 130, 140 that are operably coupled to detectors.

In other alternative embodiments of the invention, the labeled nucleic acids 230, 240, 250 may be separately synthesized in four different containers, each containing a different type of labeled nucleotide precursor. The four types of labeled nucleic acids 230, 240, 250 may then be mixed together in a single chamber 110, 120, 130, 140 for analysis of labeled nucleotide 220 distances. This would require that each type of labeled nucleotide 220 be distinguishably labeled and detected. In still other alternative embodiments, labeled nucleic acids 230, 240, 250 may be synthesized in a single chamber and then separated into four chambers 110, 120, 130, 140 for detection of labeled nucleotides 220, each chamber with a detector that is tuned to detect a single type of uniquely labeled nucleotide 220. In another alternative embodiment, complementary nucleic acid strands 230, 240, 250 containing all four types of distinguishably labeled nucleotides 220 may be synthesized in a single container and then analyzed in a single chamber 110, 120, 130, 140, using a detector that can identify each of the four types of labeled nucleotides.

In certain embodiments of the invention, each of the four labeled nucleotide precursors has a unique and highly visible optical signature that is distinguishable from unlabeled nucleotides and from other types of labeled nucleotides 220. In alternative embodiments of the invention, the labeled nucleotides 220 may be labeled with bulky groups, which may also be distinguishable. The embodiments are not limited to luminescent or bulky group labels and any type of nucleotide label known in the art, such as radioactive, nuclear magnetic resonance, electron paramagnetic resonance, electron spin resonance, etc. may be used in the practice of the disclosed methods.

In various embodiments, a nucleic acid polymerase adds one nucleotide precursor at a time to the 3' end of a primer. For each cycle of elongation, a single nucleotide precursor is incorporated into the complementary strand 230, 240, 250. The incorporation of nucleotide precursors into a complementary strand 230, 240, 250 will be determined by Watson-Crick base pair interactions with the template strand 200. Thus, the sequence of the template strand 200 may be determined from the sequence 210 of the complementary strand 230, 240, 250.

In certain embodiments of the invention the labeled nucleotides 220 in the complementary strand 230, 240, 250 will have bulky groups attached to them. The bulky groups may be attached by cross-linking or by any other method known in the art. For example, nucleotide precursors containing attached bulky groups may be incorporated into a complementary nucleic acid strand 230, 240, 250 during synthesis. Alternatively, nucleotide precursors containing a particular reactive group may be incorporated into a complementary strand 230, 240, 250, and the bulky group added by cross-linking after the complementary strand 230, 240, 250 has been synthesized. In particular embodiments of the invention the bulky groups may be any organic, inorganic or metal group or any antibody. In embodiments of the invention where metal groups are attached to labeled nucleotides 220, the metal may be a pure metal, such as gold or silver, or an alloy. In certain embodiments of the invention, the metal groups may be nanoparticles. In particular embodiments of the invention, the nanoparticles are about 1 nanometer (nm) in size, although it is contemplated that nanoparticles of about 2, 3, 4, 5, 6, 7, 8, 9 or even 10 nm or more may be used.

In certain embodiments of the invention, labeled nucleic acids 230, 240, 250 may be passed through one or more nanopores 150. Labeled nucleotides 220 may be detected by a detection unit as they pass through the nanopore 150. In a non-limiting example, a nanopore 150 may be formed by the molecule α-hemolysin. α-Hemolysin self-assembles into a lipid bilayer pore that allows a single DNA molecule to pass through unimpeded (e.g., Akeson et al., 1999, *Biophysical J.* 77:3227–323). Passage of labeled DNA through such a nanopore 150 may be detected by the effect of labeled nucleotides 220 on an ionic current within the nanopore in the presence of an applied voltage potential. Passage of a conductive label, such as a metal nanoparticle, through the nanopore 150 may be detected by an electrical detector, such as a voltage, resistance or conductivity meter. In alternative embodiments of the invention, passage of a fluorescent or luminescent label through a nanopore may be detected by an optical detector. In other alternative embodiments, a detection unit may comprise a scanning probe microscope. In embodiments of the invention where bulky groups have been attached to nucleotides, such bulky groups can be detected by scanning tunneling microscopy (STM) or atomic force microscopy (AFM). In such embodiments, the detection unit may or may not be operably coupled to a nanopore 150. Alternatively, complementary nucleic acids 230, 240, 250 labeled with bulky groups may be aligned on a surface and scanned by AFM or STM. In various embodiments, a detection unit may be operably coupled to an information processing and control system, such as a computer, to record the distances between labeled nucleotides 220.

Data for each of the reaction chambers 110, 120, 130, 140 concerning distances between labeled nucleotides 220 may be collected and analyzed (FIG. 2). A distance map 310, 320, 330, 340 may be constructed 450 for each reaction chamber 110, 120, 130, 140 and the resulting distance maps 310, 320, 330, 340 may be aligned 520 to produce a nucleic acid sequence 210 (FIG. 3). The distance maps 310, 320, 330, 340 for each reaction chamber 110, 120, 130, 140 may be constructed 450 by overlapping 420, frequency 430 and signal 440 analysis of the distances between labeled nucleotides 220. The distance maps 310, 320, 330, 340 may be aligned 520 into a sequence 210 by non-overlapping data analysis. Distance maps 310, 320, 330, 340 may be constructed 450 and aligned 520 by an information processing and control system, for example, a computer.

Certain embodiments of the invention concern synthesis of a complementary strand 230, 240, 250 of DNA. The template strand 200 can be either RNA or DNA. With an RNA template strand 200, the synthetic reagent may be a reverse transcriptase, examples of which are known in the art. In embodiments where the template strand 200 is a molecule of DNA, the synthetic reagent may be a DNA polymerase, examples of which are known in the art. In other embodiments of the invention, the complementary strand 230, 240, 250 can be a molecule of RNA. This requires that the synthetic reagent be an RNA polymerase. In these embodiments, no primer is required. However, the template strand 200 should contain a promoter that is effective to bind RNA polymerase and initiate transcription of an RNA complementary strand 230, 240, 250. Optimization of promoters is known in the art. The embodiments of the invention are not limited as to the type of template molecule 200 used, the type of complementary strand 230, 240, 250 synthesized, or the type of polymerase utilized. Virtually any template 200 and any polymerase that can support synthesis of a nucleic acid molecule complementary 230, 240, 250 in sequence 210 to the template strand 200 may be used.

In certain embodiments of the invention, the template molecule 200 may be attached to a surface such as functionalized glass, silicon, PDMS (polydimethlyl siloxane), gold, silver or other metal coated surfaces, quartz, plastic, PTFE (polytetrafluoroethylene), PVP (polyvinyl pyrrolidone), polystyrene, polypropylene, polyacrylamide, latex, nylon, nitrocellulose, a glass bead, a magnetic bead, or any other material known in the art that is capable of attaching to nucleic acids. In some embodiments of the invention, the nucleic acid molecules can be oriented on a surface as disclosed below.

In some embodiments of the invention, functional groups, such as labels, may be covalently attached to cross-linking agents so that interactions between template strand 200, complementary strand 230, 240, 250 and polymerase may occur without steric hindrance. Alternatively, the nucleic acids may be attached to surfaces using cross-linking agents. Typical cross-linking groups include ethylene glycol oligomers and diamines. Attachment may be by either covalent or non-covalent binding. Various methods of attaching nucleic acid molecules to surfaces are known in the art and may be employed.

Definitions

For the purposes of the present disclosure, the following terms have the following meanings. Terms not defined are used according to their plain and ordinary meaning.

"Antibody" includes polyclonal and monoclonal antibodies as well as fragments thereof. Antibodies also include recombinant antibodies, chemically modified antibodies and humanized antibodies, all of which can be single-chain or multiple-chain.

"Nucleic acid" means either DNA or RNA, single-stranded, double-stranded or triple stranded, as well as any modified form or analog of DNA or RNA. A "nucleic acid" may be of almost any length, from 10, 20, 30, 40, 50, 60, 75, 100, 125, 150, 175, 200, 225, 250, 275, 300, 400, 500, 600, 700, 800, 900, 1000, 1000, 2000, 2500, 3000, 3500, 4000, 4500, 5000, 6000, 7000, 8000, 9000, 10,000, 100,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule.

"Nucleotide precursor" refers to a nucleotide before it has been incorporated into a nucleic acid. In some embodiments of the invention, the nucleotide precursors are ribonucleoside triphosphates or deoxyribonucleoside triphosphates. It is contemplated that various substitutions or modifications may be made in the structure of the nucleotide precursors, so long as they are still capable of being incorporated into a complementary strand 230, 240, 250 by a polymerase. For example, in certain embodiments the ribose or deoxyribose moiety may be substituted with another pentose sugar or a pentose sugar analog. In other embodiments, the phosphate groups may be substituted, such as by phosphonates, sulphates or sulfonates. In still other embodiments, the purine or pyrimidine bases may be modified or substituted by other purines or pyrimidines or analogs thereof, so long as the sequence 210 of nucleotide precursors incorporated into the complementary strand 230, 240, 250 reflects the sequence of the template strand 200.

"Tags" or "labels" are used interchangeably to refer to any atom, molecule, compound or composition that can be used to identify a nucleotide 220 to which the label is attached. In various embodiments of the invention, such attachment may be either covalent or non-covalent. In non-limiting examples, labels may be fluorescent, phosphorescent, luminescent, electroluminescent, chemiluminescent or any bulky group or may exhibit Raman or other spectroscopic characteristics. It is anticipated that virtually any technique capable of detecting and identifying a labeled nucleotide 220 may be used, including visible light, ultraviolet and infrared spectroscopy, Raman spectroscopy, nuclear magnetic resonance, positron emission tomography, scanning probe microscopy and other methods known in the art. In certain embodiments, nucleotide precursors may be secondarily labeled with bulky groups after synthesis of a complementary strand 230, 240, 250 but before detection of labeled nucleotides 220.

The terms "a" or "an" entity may refer to one or more than one of that entity.

As used herein, "operably coupled" means that there is a functional interaction between two or more units of an apparatus 100 and/or system. For example, a detector may be "operably coupled" to a computer if the computer can obtain, process, store and/or transmit data on signals detected by the detector.

Nucleic Acids

Template molecules 200 may be prepared by any technique known to one of ordinary skill in the art. In certain embodiments of the invention, the template molecules 200 are naturally occurring DNA or RNA molecules, for example, chromosomal DNA or messenger RNA (mRNA). Virtually any naturally occurring nucleic acid may be prepared and sequenced by the disclosed methods including, without limit, chromosomal, mitochondrial or chloroplast DNA or ribosomal, transfer, heterogeneous nuclear or messenger RNA. Nucleic acids to be sequenced may be obtained from either prokaryotic or eukaryotic sources by standard methods known in the art.

Methods for preparing and isolating various forms of nucleic acids are known. (See, e.g., *Guide to Molecular Cloning Techniques,* eds. Berger and Kimmel, Academic Press, New York, N.Y., 1987; *Molecular Cloning: A Laboratory Manual,* 2nd Ed., eds. Sambrook, Fritsch and Maniatis, Cold Spring Harbor Press, Cold Spring Harbor, N.Y., 1989). Any method for preparation of template nucleic acids 200 known in the art may be used in the disclosed methods.

Labeled Nucleotide Precursors

Each reaction chamber 110, 120, 130, 140 may contain a labeled nucleotide precursor in order to produce randomly labeled complementary strands 230, 240, 250. Nucleotide precursors covalently attached to a variety of labels, such as fluorescent labels, may be obtained from standard commercial sources (e.g., Molecular Probes, Inc., Eugene, Oreg.). Alternatively, labeled nucleotide precursors may be prepared by standard techniques well known in the art. Any known method for preparing labeled nucleotide precursors may be used in the practice of the claimed subject matter.

In a non-limiting example, the percentage of labeled nucleotide precursors added to a reaction chamber 110, 120, 130, 140 is 10%, although it is contemplated that the percentage of labeled nucleotide precursors in a reaction chamber 110, 120, 130, 140 may be about 0.5, 1.0, 1.5, 2.0, 2.5, 3, 4, 5, 10, 15, 20, 25, 30, 35, 40, 45, 50, 55, 60, 65, 70, 75, 80 or 85% of the total amount of the same type of nucleotide in that chamber 110, 120, 130, 140. For example, where the chamber 110 contains a labeled adenosine nucleotide precursor, the chamber 110 may contain 10% labeled adenosine nucleotide and 90% unlabeled adenosine nucleotide, along with unlabeled cytosine, guanine and thymidine nucleotides.

The use of a lower percentage of labeled nucleotide 220 results in signal stretching. The normal distance between two adjacent nucleotides is ⅓ nm. If 10% of nucleotide precursors are labeled, then the average distance between two adjacent labeled nucleotides 220 in the complementary nucleic acid 230, 240, 250 will be approximately 13.6 nm. Stretching out the distance between adjacent labeled nucleotides 220 allows detection by techniques such as conductivity measurement, spectrophotometric analysis, AFM or STM. Such methods cannot distinguish between labels that are ⅓ nm apart. A label may be detected using any detector known in the art, such as a spectrophotometer, luminometer, NMR (nuclear magnetic resonance), mass-spectroscopy, imaging systems, charge coupled device (CCD), CCD camera, photomultiplier tubes, avalanche photodiodes, AFM or STM.

In various embodiments of the invention, a nucleotide precursor with an incorporated reactive group and/or hapten may be attached to a secondary label, such as an antibody. Any type of detectable label known in the art may be used, such as Raman tags, fluorophores, chromophores, radioisotopes, enzymatic tags, antibodies, chemiluminescent, electroluminescent, affinity labels, etc. One of skill in the art will recognize that these and other known label moieties not mentioned herein can be used in the disclosed methods.

The label moiety to be used may be a fluorophore, such as Alexa 350, Alexa 430, AMCA (7-amino-4-methylcoumarin-3-acetic acid), BODIPY (5,7-dimethyl-4-bora-3a, 4a-diaza-s-indacene-3-propionic acid) 630/650, BODIPY 650/665, BODIPY-FL (fluorescein), BODIPY-R6G (6-carboxyrhodamine), BODIPY-TMR (tetramethylrhodamine), BODIPY-TRX (Texas Red-X), Cascade Blue, Cy2 (cyanine-2), Cy3, Cy5, 5-carboxyfluorescein, fluorescein, 6-JOE (2'7'-dimethoxy-4'5'-dichloro-6-carboxyfluorescein), Oregon Green 488, Oregon Green 500, Oregon Green 5, Pacific Blue, Rhodamine Green, Rhodamine Red, ROX (6-carboxy-X-rhodamine), TAMRA (N,N,N',N'-tetramethyl-6-carboxyrhodamine), tetramethylrhodamine, and Texas Red. Fluorescent or luminescent labels can be obtained from standard commercial sources, such as Molecular Probes (Eugene, Oreg.).

In certain embodiments of the invention, nucleotides may be labeled with a bulky group. Non-limiting examples of such bulky groups include antibodies, quantum dots and metal groups. The antibodies may be labeled with a detectable marker. The detectable marker may be selected from the group consisting of enzymes, paramagnetic materials, avidin, streptavidin or biotin, fluorophores, chromophores, chemiluminophores, heavy metals, and radioisotopes.

Metal groups used as labels may consist of one type of metal, such as gold or silver, or a mixture of metals. In particular embodiments of the invention, metal groups may comprise nanoparticles. Methods of preparing nanoparticles are known (e.g., U.S. Pat. Nos. 6,054,495; 6,127,120; 6,149,868; Lee and Meisel, *J. Phys. Chem.* 86:3391–3395, 1982; Jin et al., 2001). Nanoparticles may also be obtained from commercial sources (e.g., Nanoprobes Inc., Yaphank, N.Y.; Polysciences, Inc., Warrington, Pa.). In some embodiments, nanoparticles may be cross-linked to each other prior to attachment to nucleotides. Methods of cross-linking of nanoparticles are known in the art. (e.g. Feldheim, "Assembly of metal nanoparticle arrays using molecular bridges," The Electrochemical Society Interface, Fall, 2001, pp. 22–25.) Cross-linked nanoparticles comprising monomers, dimers, trimers, tetramers, etc. may be used, for example, to provide distinguishable mass labels for different types of nucleotides. Although nanoparticles of any size are contemplated, in specific embodiments of the invention the nanoparticles may be about 0.5 to 5 nm in diameter.

Antibodies used as bulky groups may also be labeled with nanoparticles. Gold nanoparticles are available with a maleimide functionality on the surface which allows covalent linkage to antibodies, proteins and peptides through sulfhydryl groups. (Monomaleimido NANOGOLD®, Integrated DNA Technologies, Coralville, Iowa.) Techniques to label antibodies and/or nucleotides with nanoparticles are known. For example, antibodies may be labeled with gold nanoparticles after reducing the disulfide bonds in the hinge region with a mild reducing agent, such as mercaptoethylamine hydrochloride (MEA). After separation of the reduced antibody from MEA, it can be reacted with Monomaleimido NANOGOLD®. Gel exclusion chromatography can be utilized to separate the conjugated antibody from the free gold nanoparticles. Antibody fragments can be labeled in a similar manner. Gold nanoparticles can also be attached directly to labeled nucleotide precursors that contain a thiol group.

Primers

Primers may be obtained by any method known in the art. Generally, primers are between ten and twenty bases in length, although longer primers may be employed. In certain embodiments of the invention, primers are designed to be exactly complementary to a known portion of a template nucleic acid molecule 200. In one embodiment of the invention, primers are located close to the 3' end of the template nucleic acid 200. Methods for synthesis of primers of any sequence, for example using an automated nucleic acid synthesizer employing phosphoramidite chemistry are known and such instruments may be obtained from standard sources, such as Applied Biosystems (Foster City, Calif.) or Millipore Corp. (Bedford, Mass.).

Other embodiments of the invention, involve sequencing a nucleic acid in the absence of a known primer-binding site. In such cases, it may be possible to use random primers, such as random hexamers or random oligomers of 7, 8, 9, 10, 11, 12, 13, 14, 15 bases or greater length, to initiate polymerization of a complementary strand 230, 240, 250. To avoid having multiple polymerization sites on a single template strand 200, primers besides those hybridized to the template molecule 200 near its attachment site to an immobilization surface may be removed by known methods before initiating the synthetic reaction.

Reaction Chambers

In certain embodiments of the invention, four reaction chambers 110, 120, 130, 140 are used to perform the sequencing analysis. One chamber 110, designated "A", contains labeled dATP. A second 120, designated "C", contains labeled dCTP. A third 130, designated "G", contains labeled dGTP. A fourth 140, designated "T", contains labeled dTTP (or alternatively labeled dUTP). Each reaction chamber 110, 120, 130, 140 is designed to hold the nucleic acid template 200, primer, polymerase and nucleotide precursors in an aqueous environment. In some embodiments of the invention, the nucleic acids may be attached to an immobilization surface within the reaction chamber 110, 120, 130, 140. In certain embodiments of the invention, the reaction chamber 110, 120, 130, 140 will be designed to be temperature controlled, for example by incorporation of Pelletier elements or other methods known in the art. Methods of controlling temperature for low volume liquids used in nucleic acid polymerization are known in the art (e.g., U.S. Pat. Nos. 5,038,853, 5,919,622, 6,054,263 and 6,180,372).

In certain embodiments of the invention, the reaction chambers 110, 120, 130, 140 may be operably coupled to one or more fluid channels, for example, to provide connections to a molecule dispenser, to a waste port, to a template 200 loading port, or to a source of nucleotides. All these components may be manufactured in a batch fabrication process, as known in the fields of computer chip manufacture or microcapillary chip manufacture. In some embodiments of the invention, the reaction chamber 110, 120, 130, 140 and other components of the apparatus 100 may be manufactured as a single integrated chip. Such a chip may be manufactured by methods known in the art, such as by photolithography and etching. However, the manufacturing method is not limiting and other methods known in the art may be used, such as laser ablation, injection molding, casting, or imprinting techniques. Methods for manufacture of nanoelectromechanical systems may be used for certain embodiments of the invention. (See, e.g., Craighead, Science 290:32–36, 2000.) Microfabricated chips are commercially available from sources such as Caliper Technologies Inc. (Mountain View, Calif.) and ACLARA BioSciences Inc. (Mountain View, Calif.).

The material comprising the reaction chamber 110, 120, 130, 140 and other components of the apparatus 100 may be selected to be transparent to electromagnetic radiation at excitation and emission frequencies used for the detection unit. Glass, silicon, and any other materials that are generally transparent in the visible frequency range may be used for construction of the apparatus 100. In other embodiments of the invention, portions of the apparatus 100 and/or accessory devices may be designed allow the tip of an atomic force microscope or scanning tunneling microscope to scan labeled complementary strands 230, 240, 250 to measure the distances between bulky groups.

Orientation of DNA

Complementary nucleic acid strands 230, 240, 250 labeled with bulky groups 220 may be oriented on a surface before scanning by AFM or STM. Techniques to orient nucleic acid molecules on surfaces are well known in the art. (E.g., U.S. Pat. Nos. 5,840,862; 6,054,327; 6,225,055; 6,265,153; 6,303,296; 6,344,319.) In a non-limiting example, labeled nucleic acid strands 230, 240, 250 may be synthesized. A surface, such as a silanized, gold coated or otherwise derivatized glass slide, may be immersed in the reaction chamber and one end of the labeled nucleic acids 230, 240, 250 may be allowed to bind to the surface. For example, the primers used may be covalently attached to biotin at their 5' ends and the surface may be coated with avidin or streptavidin. The surface containing bound labeled nucleic acids 230, 240, 250 is slowly withdrawn from the solution. As the meniscus of the air-liquid interface passes over the bound nucleic acids 230, 240, 250, they become oriented parallel to each other, allowing the distances between labeled nucleotides 220 to be more accurately determined by AFM or SPM scanning.

Nanopores

In certain embodiments of the invention, an apparatus 100 may comprise one or more nanopores 150. In certain embodiments of the invention, the nanopore 150 is between 1 and 10 nm in diameter. In particular embodiments, the nanopore 150 may be located within a lipid bilayer membrane. In a non-limiting example, α-hemolysin subunits may self-assemble into a 1.5 nm nanopore 150 within a lipid bilayer. A voltage potential difference of, for example, 120 volts may be applied across the lipid bilayer, allowing ions to flow through the nanopore 150. The passage of a single-stranded labeled nucleic acid 230, 240, 250 through the nanopore blocks the flow of ions, allowing the determination of distances between labeled nucleotides 220 using blockade amplitude or blockade kinetics. The fluctuation in ionic current through the nanopore 150 may be measured and recorded using an Axopatch 200B instrument (Axon Instruments, Foster City, Calif.). Data may be analyzed using pClamp6 software (Axon Instruments, Foster City, Calif.).

The embodiments of the invention are not limited by the type of nanopore 150. Any nanopore 150 known in the art may be used in the disclosed methods. A nanopore 150 of approximately 2.6 nm diameter will permit passage of a double-stranded nucleic acid molecule 230, 240, 250. In embodiments of the invention where the nucleotides 220 are labeled with bulky groups, the nanopores 150 may be larger to allow passage of labeled nucleic acids 230, 240, 250.

In certain embodiments of the invention, nanopores 150 may be constructed on a solid-state matrix, such as a silicon, silicon oxide, silicon dioxide or germanium chip, by known nanolithography methods, including but not limited to chemical vapor deposition, electrochemical deposition, chemical deposition, electroplating, thermal diffusion and evaporation, physical vapor deposition, sol-gel deposition, focused electron beam, focused ion beam, molecular beam epitaxy, dip-pen nanolithography, reactive-ion beam etching, chemically assisted ion beam etching, microwave assisted plasma etching, electro-oxidation, scanning probe methods, chemical etching, laser ablation, or any other method known in the art (E.g., U.S. Pat. No. 6,146,227).

In various embodiments of the invention, the nanopore 150 may penetrate one or more sensor layers within a chip. Sensor layers may comprise semiconductor materials including, but not limited to; silicon, silicon dioxide, germanium, gallinium arsenide, and metal-based compositions such as metals or metal oxides. In some embodiments of the invention, sensor layers may be processed by electronic beam, ion beam and/or laser lithography and etching to create a channel, groove, or hole. In other embodiments of the invention, the channel, hole or groove may be coated with an organic or inorganic deposit to reduce the diameter of the channel, hole or groove, or to provide a particular type of surface, such as hydrophilic. Conducting sensor layers comprising metals may be deposited onto a semiconductor surface by means of field evaporation from a scanning tunnel microscopy (STM) or atomic force microscopy (AFM) tip or from a solution. Insulating sensor layers-may be formed by oxidizing the semiconductor's surface to an insulating composition.

In certain embodiments of the invention, channels or grooves may be etched into a semiconductor surface by various techniques known in the art including, but not limited to, methodologies using an STM/AFM tip in an oxide etching solution. After channels are formed, two semiconductor surfaces may be opposed to create one or more nanopores 150 that penetrate the semiconductor. In other embodiments of the invention, scanning probes, chemical etching techniques, and/or micromachining may be used to cut micrometer-dimensioned or nanometer-dimensioned pores 150 in a semiconductor substrate.

In some embodiments of the invention, nanopores 150 may be made using a high-throughput electron-beam lithography system (e.g., see world wide web at www.mdatechnology.net/techsearch.asp?articleid=510 [[http://wwwmdatechnology.net/ techsearch.asp?articleid= 510]]. Electron-beam lithography may be used to write features as small as 5 nm on silicon chips. Sensitive resists, such as polymethyl-methacrylate, coated on silicon surfaces may be patterned without use of a mask. The electron-beam array may combine a field emitter cluster with a microchannel amplifier to increase the stability of the electron beam, allowing operation at low currents. In some embodiments of the invention, the SoftMask® computer control system may be used to control electron-beam lithography of nanoscale features on a semiconductor chip substrate.

In alternative embodiments of the invention, nanopores 150 may be produced using focused atom lasers (e.g., Bloch et al., "Optics with an atom laser beam," *Phys. Rev. Lett.* 87:123–321, 2001). Focused atom lasers may be used for lithography, much like standard lasers or focused electron beams. Such techniques are capable of producing micron scale or even nanoscale structures on a chip. In other alternative embodiments of the invention, dip-pen nanolithography may be used to form nanopores 150 (e.g., Ivanisevic et al., "Dip-Pen Nanolithography on Semiconductor Surfaces," *J. Am. Chem. Soc.,* 123: 7887–7889, 2001). Nanopores 150 may be formed by using dip-pen nanolithography in combination with regular photolithography techniques.

In other embodiments of the invention, ion-beam lithography may be used to create nanopores 150 on a chip (e.g., Siegel, "Ion Beam Lithography," VLSI Electronics, Microstructure Science, Vol. 16, Einspruch and Watts eds., Academic Press, New York, 1987). A finely focused ion beam may be used to write nanoscale features directly on a layer of resist without use of a mask. Alternatively, broad ion beams may be used in combination with masks to form features as small as 100 nm in scale. Chemical etching, for example, with hydrofluoric acid, may be used to remove exposed silicon or other chip material that is not protected by resist. The skilled artisan will realize that the techniques disclosed above are not limiting, and that nanopores 150 may be formed by any method known in the art.

Detection Unit

The embodiments of the invention are not limited by the type of detection unit used, and any known detection unit may be used in the disclosed methods and apparatus 100.

SPM Detectors

In certain embodiments of the invention a detection unit may comprise a scanning probe microscope (SPM). In particular embodiments of the invention a detection unit may comprise a scanning tunneling microscope (STM). A STM in the constant-current mode will measure irregular surfaces, such as nucleotides labeled 220 with bulky groups, and the distance between such labels 220 can be measured and recorded. A STM scans a sample with a narrow metallic tip, sharpened to a single atom point, which is physically connected to the scanner by means of piezoelectric materials to allow investigation of electrically conducting surfaces down to an atomic scale. This is accomplished by applying a small bias voltage between the tip and the sample. If the distance between the two is large, there will be no current flow between them. In contrast, when the tip is brought very close to the sample without physical contact, there will be current flowing between the two. The measurement of such current between the tip and the sample allows the atomic information of the surface of a DNA molecule to be mapped in order to determine the distances between bulky groups attached to labeled nucleotides 220 as they pass under the tip.

In another embodiment of the invention, a detection unit may comprise an atomic force microscope (AFM). With conductive AFM, the tip stays in contact with the sample and a cantilever deflection signal is used to maintain a constant force between the tip and the sample in order to generate topographic images. While a DC bias is applied to the tip, the sample is held at ground potential and the pre-amplifier in the scanner head measures the current passing through the tip and the sample in order to generate the image. This allows a base distance map 310, 320, 330, 340 to be constructed from the distance measured between bulky groups attached to the labeled nucleotides 220 as they pass under the tip.

In alternative embodiments of the invention a detection unit may comprise other SPMs such as magnetic force microscopy, lateral force microscopy, force modulation microscopy, phase detection microscopy, electrostatic force microscopy, scanning thermal microscopy, near-field scanning optical microscopy, pulsed force mode and microthermal analysis. Methods of use of such detection units are well known in the art.

Electrical Detectors

In some embodiments of the invention, an electrical detector may be operably coupled to one or more conducting layers, a power supply and one or more nanopores 150 perpendicular to and penetrating the conducting layers. The detector may comprise an ammeter, voltmeter, capacitance meter and/or conductivity meter to measure induced current, voltage, resistance, etc. In certain embodiments, other electrical components such as resistors or capacitors may be included in the electrical circuit associated with the detector.

In some embodiments of the invention, the reaction chambers 110, 120, 130, 140 may be filled with a low conductivity aqueous buffer. An electrical potential may be applied to the conducting layers flanking a nanopore 150. When buffer alone is present in the nanopore 150, the resistance between the conducting layers is high. The presence of unlabeled regions of nucleic acids passing through the nanopore 150 would produce a slight increase in conductivity across the nanopore 150. The passage of nucleotides 220 labeled with highly conductive labels, such as metal nanoparticles, would result in a large increase in conductivity that produces a detectable signal at the detector. The time interval between signals may be measured and used to determine distances between labeled nucleotides 220.

In particular embodiments of the invention, current across the nanopore 150 may be converted to voltage and amplified using an Axopatch 200A (Axon Instruments, Foster City, Calif.) or a Dagan 3900A patch clamp amplifier (Dagan Instruments, Minneapolis, Minn.). The signal may be filtered using a Frequency Devices (Haverhill, Mass.) low pass Bessel filter. Data may be digitized using a National Instruments (Austin, Tex.) AT-MIO-16-X 16-bit board and LAB WINDOWS/CVI programs. The chip may be shielded from electric and magnetic noise sources using a mu-metal box (Amuneal, Philadelphia, Pa.)

Spectrophotometric Detectors

In alternative embodiments of the invention, labeled nucleotides 220 attached to luminescent labels may be detected using a light source and photodetector, such as a diode-laser illuminator and fiber-optic or phototransistor detector. (E.g., Sepaniak et al., J. Microcol. Separations 1:155–157, 1981; Foret et al., Electrophoresis 7:430–432, 1986; Horokawa et al., J. Chromatog. 463:39–49 1989; U.S. Pat. No. 5,302,272.) Other exemplary light sources include vertical cavity surface-emitting lasers, edge-emitting lasers, surface emitting lasers and quantum cavity lasers, for example a Continuum Corporation Nd-YAG pumped Ti:Sapphire tunable solid-state laser and a Lambda Physik excimer pumped dye laser. Other exemplary photodetectors include photodiodes, avalanche photodiodes, photomultiplier tubes, multianode photomultiplier tubes, phototransistors, vacuum photodiodes, silicon photodiodes, and charge-coupled devices (CCDs).

In some embodiments of the invention, the photodetector, light source, and nanopore 150 may be fabricated into a semiconductor chip using known N-well Complementary Metal Oxide Semiconductor (CMOS) processes (Orbit Semiconductor, Sunnyvale, Calif.). In alternative embodiments of the invention, the detector, light source and nanopore 150 may be fabricated in a silicon-on-insulator CMOS process (e.g., U.S. Pat. No. 6,117,643). In other embodiments of the invention, an array of diode-laser illuminators and CCD detectors may be placed on a semiconductor chip (U.S. Pat. Nos. 4,874,492 and 5,061,067; Eggers et al., BioTechniques 17: 516–524, 1994).

In certain embodiments of the invention, a highly sensitive cooled CCD detector may be used. The cooled CCD detector has a probability of single-photon detection of up to 80%, a high spatial resolution pixel size (5 microns), and sensitivity in the visible through near infrared spectra. (Sheppard, Confocal Microscopy: Basic Principles and System Performance in: Multidimensional Microscopy, P.C. Cheng et al. eds., Springer-Verlag, New York, N.Y. pp. 1–51, 1994.) In another embodiment of the invention, a coiled image-intensified coupling device (ICCD) may be used as a photodetector that approaches single-photon counting levels (U.S. Pat. No. 6,147,198). A small number of photons triggers an avalanche of electrons that impinge on a phosphor screen, producing an illuminated image. This phosphor image is sensed by a CCD chip region attached to an amplifier through a fiber optic coupler. In some embodiments of the invention, a CCD detector on a chip may be sensitive to ultraviolet, visible, and/or infrared spectra light (U.S. Pat. No. 5,846,708).

In some embodiments of the invention, a nanopore 150 may be operably coupled to a light source and a detector on a semiconductor chip. In certain embodiments of the invention, the detector may be positioned perpendicular to the light source to minimize background light. The photons generated by excitation of a luminescent label may be collected by a fiber optic. The collected photons are transferred to a CCD detector and the light detected and quantified. The times at which labeled nucleotides 220 are detected may be recorded and nucleotide distance maps 310, 320, 330, 340 may be constructed. Methods of placement of optical fibers on a semiconductor chip in operable contact with a CCD detector are known (U.S. Pat. No. 6,274,320).

In some embodiments of the invention, an avalanche photodiode (APD) may be made to detect low light levels. The APD process uses photodiode arrays for electron multiplication effects (U.S. Pat. No. 6,197,503). In other embodiments of the invention, light sources, such as light-emitting diodes (LEDs) and/or semiconductor lasers may be incorporated into semiconductor chips (U.S. Pat. No. 6,197,503). Diffractive optical elements that shape a laser or diode light beam may also be integrated into a chip.

In certain embodiments of the invention, a light source produces electromagnetic radiation that excites a photosensitive label, such as fluorescein, attached to a nucleic acid. In some embodiments of the invention, an air-cooled argon laser at 488 nm excites fluorescein-labeled nucleic acid molecules 230, 240, 250. Emitted light may be collected by a collection optics system comprising a fiber optic, a lens, an imaging spectrometer, and a 0° C. thermoelectrically-cooled CCD camera. Alternative examples of fluorescence detectors are known in the art (e.g., U.S. Pat. No. 5,143,8545).

Determination of Nucleic Acid Sequence

Figure 4:
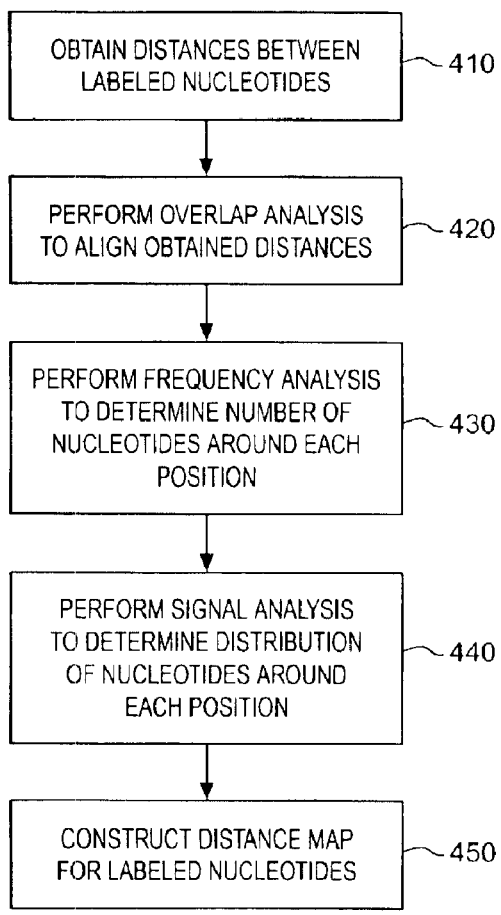
FIG. 4 illustrates an exemplary method for constructing 450 distance maps (see FIG. 3, distance map 310, 320, 330, 340) for labeled nucleotides 220.
Figure 5:
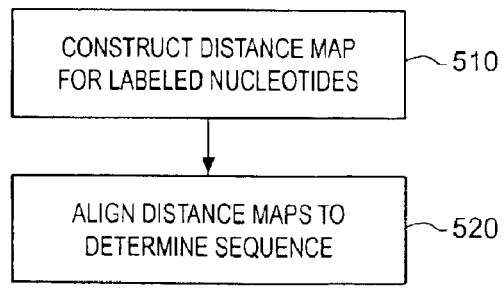
FIG. 5 illustrates an exemplary method for aligning 520 distance maps (see FIG. 3, distance map 310, 320, 330, 340) to obtain a nucleic acid sequence (see FIG. 2 nucleic acid sequence 210) of the complementary strand (see FIG. 2, complementary strand 230, 240, 250).

In some embodiments of the invention, determining the sequence 210 of complementary nucleic acids 230, 240, 250 includes constructing 450 distance maps 310, 320, 330, 340 for each type of labeled nucleotide 220 and aligning 520 the distance maps 310, 320, 330, 340 to produce the complete sequence 210 (FIG. 4 and FIG. 5). The sequence of the template nucleic acid 200 will be exactly complementary to the determined sequence 210. In an exemplary embodiment, a distance map 310, 320, 330, 340 for each type of labeled nucleotide 220 is constructed 450 according to the process of FIG. 4. Random labeling and detection of labeled nucleotides 220 is performed on the complementary strands 230, 240, 250, resulting in a percentage of the nucleotides in each strand 230, 240, 250 being labeled 220. The percentage of labeled nucleotides 220 may vary depending on the labeling and detection schemes used. In one embodiment, about 10% of the nucleotides of the same type on a complementary strand 230, 240, 250 are labeled 220, in order to ensure easily detectable distances between labeled nucleotides 220. After synthesis of labeled complementary strands 230, 240, 250, the distances between labeled nucleotides 220 are obtained 410 (FIG. 2). The obtained distances 410 between labeled nucleotides 220 are represented graphically in FIG. 2. The obtained distances 410 may be used to construct 450 distance maps 310, 320, 330, 340 for each type of labeled nucleotide 220.

In various embodiments of the invention, overlap analysis is performed 420 on the obtained distances. This serves to align the distances so that the complementary strands 230, 240, 250 begin and end at the same place. In one embodiment, the overlap analysis 420 includes maximizing position overlaps. Since a large number of complementary strands 230, 240, 250 are used, each nucleotide in the sequence 210 will be labeled a large number of times in different complementary strands 230, 240, 250. Therefore, maximizing the overlaps will align the obtained distances 420 so that the positions of labeled nucleotides 220 on each complementary strand 230, 240, 250 correspond. Alternate methods, such as uniquely labeling the beginning or the end of the complementary strands 230, 240, 250, may be used instead of or in addition to overlap analysis to align the obtained distances 420. After the obtained distances are aligned 420, frequency analysis may be performed 430 to determine the number of labeled nucleotides 220 around each labeled position. In one embodiment, using the law of large numbers and the independent and uniform nature of the labeling and detection processes, it can be inferred that a labeled nucleotide 220 in each position is labeled with approximately the same probability on each complementary strand 230, 240, 250 as the probability of being labeled on a single strand. Thus, in the example using 10% labeled nucleotides 220, if 1000 strands 230, 240, 250 are used, the number of times a nucleotide at a single position is labeled 220 should be 10% of 1000, or 100 times.

Using this observation, the number of labeled nucleotides 220 that are too close for independent detection can be determined. For example, using 10% labeling probability and 1000 labeled complementary strands 230, 240, 250, if 102 strands 230, 240, 250 show a labeled nucleotide 220 at a given position, then it can be inferred that that position is occupied by one labeled nucleotide 220, with no other labeled nucleotides 220 so close that detection errors occur. On the other hand, if 197 strands 230, 240, 250 show a labeled nucleotide 220 at the given position, it can be inferred that there are two labeled nucleotides 220 present, one in the given position and a second too close to accurately measure. The labeled nucleotides 220 of the same type may be contiguous with each other or may be spaced apart by one or more nucleotides of a different type. The same analysis applies where two or more nucleotides of the same type are located in adjoining positions. Where two adjacent nucleotides are identical, the position would be expected to be labeled about twice as often, three adjacent identical nucleotides should be labeled about three times as often, etc.

When it is determined that two or more labeled nucleotides 220 are located too close together for independent measurement, signal analysis may be performed 440 to determine the spatial relationship. For example, the signal produced by two labeled nucleotides 220 separated by one other nucleotide may be different from the signal produced by two contiguous labeled nucleotides 220, or two labeled nucleotides 220 separated by two other nucleotides. Other methods may also be used to distinguish the spatial relationship between closely spaced identical nucleotides. In certain embodiments of the invention, frequency analysis may be performed 430 to determine the relative positions of labeled nucleotides 220. For example, to distinguish between three labeled nucleotides 220 in a row and two labeled nucleotides 220 separated by one other nucleotide, one signal should occur only two-thirds as often as the other signal. Frequency and signal analysis may be performed in any order in the claimed methods.

As disclosed in FIG. 4 and FIG. 5, a distance map 310, 320, 330, 340 for each type of labeled nucleotide 220 may be constructed 450. Although all four types of nucleotides may be labeled 220 and distance maps 310, 320, 330, 340 constructed 450, in alternative embodiments of the invention only three of the four types of nucleotides may be labeled 220 and analyzed. In such embodiments, the positions of the fourth type of nucleotide may be inferred by gaps in the aligned 520 distance maps 310, 320, 330, 340 of the other three types of nucleotide. The complete nucleic acid sequence 210 may be determined by aligning 520 the distance maps 310, 320, 330, 340 for the different types of labeled nucleotides 220. In certain embodiments of the invention, the distance maps 310, 320, 330, 340 may be aligned 520 using the non-overlapping rule. According to that rule, two different nucleotides cannot occupy the same position in the sequence 210.

In some embodiments of the invention, distance maps 310, 320, 330, 340 may be aligned 520 one at a time, beginning with the distance map 310, 320, 330, 340 with the greatest number of labeled nucleotides 220. If more than one possible alignment is found, the alignment producing the shortest sequence 210 is chosen, according to the rule of minimum sequence 210 length. If additional distance maps 310, 320, 330, 340 cannot be aligned 520 without overlap, the alignments may be iteratively reevaluated until an alignment without overlap is obtained. If no alignment of the distance maps 310, 320, 330, 340 exists such that the non-overlap rule is completely observed, then alternative constructions 450 of the distance maps 310, 320, 330, 340 may also be iteratively reevaluated until a non-overlapping sequence 210 is obtained.

In certain embodiments of the invention, the sequencing process may produce a perfectly aligned sequence 210 for most of the nucleic acid, with one or more short segments where overlap occurs or where the sequence 210 is otherwise ambiguous. The operator may review the data at any point in the analysis and conclude that either the entire nucleic acid should be sequenced again, or that only-short regions of the, nucleic acid template 200 should be resequenced. Such evaluation of the results of sequence 210 analysis is well within the ordinary skill in the art, as is known with existing methods of nucleic acid sequencing. This determination may be made automatically by a computer based on statistical analysis of the data, or by a human user.

In another embodiment of the invention, the beginning and ends of the distance maps 310, 320, 330, 340 as they relate to the sequence 210 may be known. In this case, the alignment 520 may include lining up the known ends of the distance maps 310, 320, 330, 340.

Information Processing and Control System and Data Analysis

In certain embodiments of the invention, the sequencing apparatus 100 may comprise an information processing and control system. The embodiments are not limiting for the type of information processing and control system used. An exemplary information processing and control system may incorporate a computer comprising a bus for communicating information and a processor for processing information. In one embodiment of the invention, the processor is selected from the Pentium® family of processors, including without limitation the Pentium® II family, the Pentium® III family and the Pentium® 4 family of processors available from Intel Corp. (Santa Clara, Calif.). In alternative embodiments of the invention, the processor may be a Celeron®, an Itanium®, a Pentium Xeon® or an X-scale processor (Intel Corp., Santa Clara, Calif.). In various other embodiments of the invention, the processor may be based on Intel® architecture, such as Intel® IA-32 or Intel® IA-64 architecture. Alternatively, other processors may be used.

The computer may further comprise a random access memory (RAM) or other dynamic storage device, a read only memory (ROM) and/or other static storage and a data storage device such as a magnetic disk or optical disc and its corresponding drive. The information processing and control system may also comprise other peripheral devices known in the art, such a display device (e.g., cathode ray tube or Liquid Crystal Display), an alphanumeric input device (e.g., keyboard), a cursor control device (e.g., mouse, trackball, or cursor direction keys) and a communication device (e.g., modem, network interface card, or interface device used for coupling to Ethernet, token ring, or other types of networks).

In particular embodiments of the invention, the detection unit may also be coupled to the bus. Data from the detection unit may be processed by the processor and the data stored in the main memory. The processor may calculate distances between labeled nucleotides 220, based on the time intervals between detection of labeled nucleotides 220. Nucleotide distances may be stored in main memory and used by the processor to construct 450 distance maps 310, 320, 330, 340 for each reaction chamber 110, 120, 130, 140. The processor may also align 520 the distance maps 310, 320, 330, 340 to generate a complementary nucleic acid sequence 210, from which a template nucleic acid sequence 200 may be derived.

It is appreciated that a differently equipped information processing and control system than the example described above may be used for certain implementations. Therefore, the configuration of the system may vary in different embodiments of the invention. It should also be noted that, while the processes described herein may be performed under the control of a programmed processor, in alternative embodiments of the invention, the processes may be fully or partially implemented by any programmable or hardcoded logic, such as Field Programmable Gate Arrays (FPGAs), TTL logic, or Application Specific Integrated Circuits (ASICs), for example. Additionally, the method may be performed by any combination of programmed general purpose computer components and/or custom hardware components.

In certain embodiments of the invention, custom designed software packages may be used to analyze the data obtained from the detection unit. In alternative embodiments of the invention, data analysis may be performed, using an information processing and control system and publicly available software packages. Non-limiting examples of available software for DNA sequence 210 analysis include the PRISM™ DNA Sequencing Analysis Software (Applied Biosystems, Foster City, Calif.), the Sequencher™ package (Gene Codes, Ann Arbor, Mich.), and a variety of software packages available through the National Biotechnology Information Facility at website www.nbif.org/links/1.4.1.php.

EXAMPLES

The following examples are included to demonstrate particular embodiments of the invention. However, those of skill in the art should, in light of the present disclosure, will appreciate that many changes can be made in the specific details which are disclosed and still obtain a like or similar result without departing from the claimed subject matter.

Example 1

DNA Sequencing

Digest 1.2 µg of genomic DNA with a restriction enzyme to enable isolation of a fragment of interest. There may be approximately 400,000 copies of the fragment of interest. The amount of genomic DNA to be digested can be increased to equate to 400,000 copies. Divide the isolated fragment into 4 sub-samples designated A,G,T and C. There may be approximately 100,000 copies of the fragment of interest in each reaction chamber 110, 120, 130, 140. Denature each DNA sub-sample and then anneal a specific oligonucleotide primer with a biotin on the 5' end of the primer. Add 200 µM dATP, dCTP, dGTP, dTTP and DNA polymerase to each reaction chamber 110, 120, 130, 140. In addition, add 20 µM of thiol-derivatized nucleotide precursor to each reaction chamber 110, 120, 130, 140. For example, the first chamber 110 will contain 20 µM of thiol-dATP, the second 120 will contain 20 µM of thiol-dCTP, the third 130 will contain 20 µM of thiol-dGTP and the fourth 140 will contain 20 µM of thiol-dTTP. Generate complementary strands 230, 240, 250 of DNA that incorporate the derivatized nucleotide precursors. Cross-link 1 nm gold particles to the derivatized nucleotides and separate free gold particles from gold particles cross-linked to labeled nucleotides 220 by washing.

Allow the DNA complementary strands 230, 240, 250 to bind to streptavidin immobilized on one side of a flat surface. Orient molecules by "molecular combing" and immobilize the fixed DNA molecules on the flat surface (see U.S. Pat. Nos. 5,840,862; 6,054,327; 6,225,055; 6,265,153; 6,303,296; 6,344,319).

Scan the complementary strands 230, 240, 250 of DNA for gold particles by STM or AFM and record the distance between gold particles on labeled nucleotides 220. Repeat the scanning process for multiple labeled nucleic acids 230, 240, 250 to obtain overlapping sets of labeled nucleotide 220 distances in each reaction chamber 110, 120, 130, 140. Each set of labeled nucleotide 220 distances represents the distance measurements for a single labeled nucleic acid 230, 240, 250.

Construct 450 a base distance map 310, 320, 330, 340 for each reaction chamber 110, 120, 130, 140 by combining all of the measured distances between labeled nucleotides 220 from complementary strands 230, 240, 250 in that reaction chamber 110, 120, 130, 140. Use an algorithm that assesses the overlap 420 between all of the measured distances, the frequency 430 of signals and signal analysis 440 to construct 450 the distance maps 310, 320, 330, 340. The computer program should search to find the maximum and most uniform overlap among all of the scanned complementary strands 230, 240, 250 of DNA.

Assemble a DNA sequence 210 by aligning 520 the four distance maps 310, 320, 330, 340 and eliminating overlap. A computer program may be used to complete this function. When aligning 520 the distance maps 310, 320, 330, 340, it may be useful to find the distance map 310, 320, 330, 340 with the greatest number of bases and the map 310, 320, 330, 340 with the second highest number of bases and align 520 those. When aligning 520 the maps 310, 320, 330, 340, the non-overlap rule and the rule of minimum sequence 210 length should be utilized. The computer should find only one possible fit. Next align 520 a third distance map 310, 320, 330, 340. Use the non-overlap rule and the rule of minimum sequence 210 length to merge this distance map 310, 320, 330, 340 into the previously merged map 310, 320, 330, 340. Do the same thing for the fourth distance map 310, 320, 330, 340 to generate a complete nucleic acid sequence 210. Where aligned distance maps 310, 320, 330, 340 result in two or more different types of nucleotides located at the same position on the sequence 210, repeat the alignment process using a different alignment. The data analysis is completed when a sequence 210 is generated that has no overlapping bases and no gaps in the sequence 210.

All of the COMPOSITIONS, METHODS and APPARATUS 100 disclosed and claimed herein can be made and executed without undue experimentation in light of the present disclosure. While the disclosed compositions, methods and apparatus 100 have been described in terms of specific embodiments of the invention, it will be apparent to those of skill in the art that variations may be applied without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the claimed subject matter as defined by the appended claims.

---

What is claimed is:

1. A method comprising:
   (a) obtaining at least four samples comprising a template nucleic acid;
   (b) individually incubating the samples of (a) under conditions suitable for synthesizing a nucleic acid sequence complementary to the template nucleic acid, wherein the complementary sequence comprises a type of nucleotide precursor specific to a particular sample and structurally suitable for attachment to a bulky group;
   (c) labeling the nucleotide precursor of (b) by attaching a bulky group to at least a portion of the nucleotide precursors;
   (d) prior to, simultaneous with, or subsequent to (c), orienting each complementary nucleic acid sequence generated in (b) such that distances between bulky groups can be measured;
   (e) measuring the distances between the bulky groups associated with each contiguous complementary sequence in each sample and identifying overlapping distances, wherein the distance is measured by scanning probe microscopy;
   (f) constructing a distance map for each sample based upon the measurements generated in (e);
   (g) aligning the distance maps of (f);
   (h) assembling a nucleic acid sequence of the complementary sequence; and
   (i) determining the sequence of the template nucleic acid based on the sequence of the complementary sequence.

2. The method of claim 1, further comprising analyzing the measured distances by overlapping data analysis and frequency analysis to construct the distance maps.

3. The method of claim 1, wherein the distance maps are assembled into a sequence by non-overlapping data analysis.

4. The method of claim 1, wherein the conditions suitable for synthesizing a nucleic acid sequence complementary to the template nucleic acid sequence comprise hybridizing oligonucleotide primers to the template nucleic acids and contacting the template/oligonucleotide complexes with a polymerase.

5. The method of claim 4, wherein the 5' end of the oligonucleotide primers comprises biotin.

6. The method of claim 5, wherein prior to, simultaneously with, or subsequent to synthesis, the oligonucleotide comprising biotin is attached to a surface comprising streptavidin and/or avidin.

7. The method of claim 1, wherein the bulky groups are attached to the nucleotides before or after synthesis of the complementary nucleic acid strands.

8. The method of claim 7, wherein the bulky groups are selected from the group consisting of organic groups, quantum dots, antibodies and metallic groups.

9. The method of claim 8, wherein the metallic group is a nanoparticle.

10. The method of claim 9, wherein the nanoparticles are gold or silver, said nanoparticles between about 0.5 and 5.0 nanometer (nm) in size.

11. The method of claim 1, wherein the distance between bulky groups is measured by atomic force microscopy or scanning tunneling microscopy.

12. The method of claim 1, wherein each sample comprises about 100,000 copies of the template nucleic acid.

13. A method comprising:
   (a) introducing samples comprising a template nucleic acid and placing into at least four chambers;
   (b) individually incubating the samples of (a) under conditions suitable for synthesizing a nucleic acid sequence complementary to the template nucleic acids, wherein the complementary sequence comprises a type of nucleotide precursor specific to a particular sample and structurally suitable for attachment to a conductive label;
   (c) labeling the nucleotide precursor of (b) by attaching a conductive label to at least a portion of the nucleotide precursors;
   (d) prior to, simultaneous with, or subsequent to (c), orienting each complementary nucleic acid sequence generated in (b) such that distances between bulky groups can be measured;
   (e) orienting and translocating the complementary nucleic acid sequences through nanopores operably coupled to a detectors that detect the conductive label;

(f) measuring the distances between labeled nucleotides associated with a contiguous complementary sequence in each sample and identifying overlapping distances;

(g) constructing a distance map for the complementary nucleic acid sequences in each chamber, wherein the distance map is based upon the measurements generated in (f);

(h) aligning the distance maps of (g);

(i) assembling a nucleic acid sequence of the complementary sequence; and (j) determining the sequence of the template nucleic acid.

14. The method of claim 13, further comprising analyzing the measured distances by overlapping data analysis and frequency analysis to construct the distance maps.

15. The method of claim 13, wherein the distance maps are assembled into a sequence by non-overlapping data analysis.

16. The method of claim 13, wherein the nanopores are between 1 nm and 50 nm in diameter.

17. The method of claim 16, wherein the nanopores are between 3 nm and 10 nm in diameter.

18. The method of claim 16, wherein the nanopore diameter is selected to allow a single labeled nucleic acid strand to pass through a single nanopore at one time.

19. The method of claim 18, wherein the labeled nucleic acid strand is hybridized to a template nucleic acid.

20. The method of claim 13, wherein at least one end of each nucleic acid strand is attached to a distinguishable label.

21. The method of claim 13, wherein the conductive label is a metal nanoparticle.

22. The method of claim 13, wherein the detector is selected from the group consisting of a voltage meter, a resistance meter, and a conductivity meter.

23. An apparatus comprising:

(a) at least four reaction chambers, each chamber to contain a type of nucleotide precursor specific to a particular chamber and structurally suitable for attachment to a conductive label;

(b) multiple nanopores in each reaction chamber; and (c) a detector operably coupled to each nanopore, wherein the detector detects a conductive label.

24. The apparatus of claim 23, further comprising: (i) an information processing system; and (ii) a database.

25. The apparatus of claim 23, wherein the conductive label is a metal nanoparticles attached to labeled nucleic acid strands.

26. The apparatus of claim 23, wherein the reaction chambers and nanopores are part of an integrated chip.

27. The apparatus of claim 23, wherein the detector is selected from the group consisting of a voltage meter, a resistance meter, and a conductivity meter.

* * * * *